US009089571B2

(12) United States Patent
Solca et al.

(10) Patent No.: US 9,089,571 B2
(45) Date of Patent: Jul. 28, 2015

(54) QUINAZOLINE DERIVATIVES FOR THE TREATMENT OF CANCER DISEASES

(71) Applicants: Flavio Solca, Vienna (AT); Andree Amelsberg, Southbury, CT (US); Jacobus C. A. van Meel, Moedling (AT); Anke Baum, Hinterbruehl (AT); Gerd Stehle, Ehingen (DE)

(72) Inventors: Flavio Solca, Vienna (AT); Andree Amelsberg, Southbury, CT (US); Jacobus C. A. van Meel, Moedling (AT); Anke Baum, Hinterbruehl (AT); Gerd Stehle, Ehingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/766,914

(22) Filed: Feb. 14, 2013

(65) Prior Publication Data

US 2013/0178487 A1 Jul. 11, 2013

Related U.S. Application Data

(63) Continuation of application No. 12/093,321, filed as application No. PCT/EP2006/068313 on Nov. 9, 2006, now Pat. No. 8,404,697.

(30) Foreign Application Priority Data

Nov. 11, 2005 (EP) ..................... 05110656

(51) Int. Cl.
*A61K 31/517* (2006.01)
*A61K 31/553* (2006.01)

(52) U.S. Cl.
CPC ............. *A61K 31/517* (2013.01); *A61K 31/553* (2013.01)

(58) Field of Classification Search
None
See application file for complete search history.

(56) References Cited

U.S. PATENT DOCUMENTS

| | | | |
|---|---|---|---|
| 4,933,443 A | 6/1990 | Hamashima et al. |
| 5,728,687 A | 3/1998 | Bissery |
| 5,866,572 A | 2/1999 | Barker et al. |
| 6,127,374 A | 10/2000 | Bridges |
| 6,153,617 A | 11/2000 | Bridges |
| 6,251,912 B1 | 6/2001 | Wissner et al. |
| 6,297,258 B1 | 10/2001 | Wissner et al. |
| 6,344,459 B1 | 2/2002 | Bridges et al. |
| 6,362,336 B1 | 3/2002 | Lohmann et al. |
| 6,403,580 B1 | 6/2002 | Himmelsbach et al. |
| 6,617,329 B2 | 9/2003 | Himmelsbach et al. |
| 6,627,634 B2 | 9/2003 | Himmelsbach et al. |
| 6,653,305 B2 | 11/2003 | Himmelsbach et al. |
| 6,656,946 B2 | 12/2003 | Himmelsbach et al. |
| 6,673,803 B2 | 1/2004 | Thomas et al. |
| 6,740,651 B2 | 5/2004 | Himmelsbach et al. |
| 6,924,285 B2 | 8/2005 | Himmelsbach et al. |
| 6,972,288 B1 | 12/2005 | Himmelsbach et al. |
| 7,019,012 B2 | 3/2006 | Himmelsbach et al. |
| 7,084,136 B2 | 8/2006 | Tanimoto et al. |
| 7,119,084 B2 | 10/2006 | Himmelsbach et al. |
| 7,160,889 B2 | 1/2007 | Hennequin et al. |
| 7,196,091 B2 | 3/2007 | Himmelsbach et al. |
| 7,220,750 B2 | 5/2007 | Himmelsbach et al. |
| 7,223,749 B2 | 5/2007 | Himmelsbach et al. |
| 7,456,189 B2 | 11/2008 | Himmelsbach et al. |
| 7,846,936 B2 | 12/2010 | Hilberg et al. |
| 7,960,546 B2 | 6/2011 | Schroeder et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 8,404,697 B2 | 3/2013 | Solca et al. |
| 2001/0044435 A1 | 11/2001 | Himmelsbach et al. |
| 2002/0032208 A1 | 3/2002 | Lohmann et al. |
| 2002/0077330 A1 | 6/2002 | Himmelsbach et al. |
| 2002/0082270 A1 | 6/2002 | Himmelsbach et al. |
| 2002/0169180 A1 | 11/2002 | Himmelsbach et al. |
| 2002/0173509 A1 | 11/2002 | Himmelsbach et al. |
| 2003/0149062 A1 | 8/2003 | Jung et al. |
| 2003/0186956 A1 | 10/2003 | Bilke et al. |
| 2003/0191308 A1 | 10/2003 | Hennequin et al. |

(Continued)

FOREIGN PATENT DOCUMENTS

| | | | |
|---|---|---|---|
| DE | 19825591 A1 | 12/1999 |
| DE | 19908567 A1 | 8/2000 |
| DE | 19911366 A1 | 9/2000 |
| DE | 10017539 A1 | 10/2001 |
| DE | 10042060 A1 | 3/2002 |

(Continued)

OTHER PUBLICATIONS

"Afatinib Prolongs Progression-Free Survival in NSCLC", 2012 ASCO Annual Meeting, Chicago, ASCO Daily News, LBA7500, Jun. 1-5, 2012. [downloaded from the internet Oct. 25, 2012. http://chicago2012.asco.org/ASCODailyNews/LBA7500.aspx].

(Continued)

*Primary Examiner* — James D Anderson
(74) *Attorney, Agent, or Firm* — Michael P. Morris; David L. Kershner (57) ABSTRACT

The present invention relates to the use of quinazolines of formula (I), (I)

wherein the groups $R^a$ to $R^d$ have the meanings given in the claims and specification, in cancer therapy.

3 Claims, 4 Drawing Sheets

(56) References Cited

U.S. PATENT DOCUMENTS

| | | |
|---|---|---|
| 2003/0225079 A1 | 12/2003 | Singer et al. |
| 2004/0024019 A1 | 2/2004 | Tanimoto et al. |
| 2004/0057992 A1 | 3/2004 | Gierer |
| 2004/0158065 A1 | 8/2004 | Barth et al. |
| 2005/0031769 A1 | 2/2005 | Watanabe et al. |
| 2005/0043233 A1 | 2/2005 | Stefanic et al. |
| 2005/0085495 A1 | 4/2005 | Soyka et al. |
| 2005/0215574 A1 | 9/2005 | Bradbury et al. |
| 2006/0058311 A1 | 3/2006 | Munzert et al. |
| 2006/0100223 A1 | 5/2006 | Himmelsbach et al. |
| 2006/0270672 A1 | 11/2006 | Himmelsbach et al. |
| 2007/0027170 A1 | 2/2007 | Soyka et al. |
| 2007/0078091 A1 | 4/2007 | Hubler et al. |
| 2007/0099918 A1 | 5/2007 | Singer et al. |
| 2007/0185091 A1 | 8/2007 | Himmelsbach et al. |
| 2008/0096212 A1 | 4/2008 | Bell et al. |
| 2008/0103161 A1 | 5/2008 | Himmelsbach et al. |
| 2008/0145422 A1 | 6/2008 | Zhou et al. |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0269487 A1 | 10/2008 | Bradbury et al. |
| 2009/0036676 A1 | 2/2009 | Himmelsbach et al. |
| 2009/0203683 A1 | 8/2009 | Himmelsbach et al. |
| 2009/0238828 A1 | 9/2009 | Munzert et al. |
| 2009/0306044 A1 | 12/2009 | Solca et al. |
| 2009/0306072 A1 | 12/2009 | Jung et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0087482 A1 | 4/2010 | Haber et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0136826 A1 | 6/2011 | Hilberg et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0107399 A1 | 5/2012 | Barta |
| 2012/0157472 A1 | 6/2012 | Larsen et al. |
| 2012/0329778 A1 | 12/2012 | Himmelsbach et al. |
| 2013/0012465 A1 | 1/2013 | Haslinger et al. |

FOREIGN PATENT DOCUMENTS

| | | |
|---|---|---|
| DE | 10042064 A1 | 3/2002 |
| EP | 0302967 A2 | 2/1989 |
| EP | 0566226 A1 | 10/1993 |
| EP | 0799619 A2 | 10/1997 |
| EP | 1123705 A1 | 8/2001 |
| WO | 9410995 A1 | 5/1994 |
| WO | 9520045 A1 | 7/1995 |
| WO | 9630347 A1 | 10/1996 |
| WO | 9633980 A1 | 10/1996 |
| WO | 9702266 A1 | 1/1997 |
| WO | 9738983 A1 | 10/1997 |
| WO | 9843960 A1 | 10/1998 |
| WO | 9906378 A1 | 2/1999 |
| WO | 9906396 A1 | 2/1999 |
| WO | 9909016 A1 | 2/1999 |
| WO | 9933980 A2 | 7/1999 |
| WO | 9935146 A1 | 7/1999 |
| WO | 9965228 A2 | 12/1999 |
| WO | 0018740 A1 | 4/2000 |
| WO | 0031048 A1 | 6/2000 |
| WO | 0031068 A1 | 6/2000 |
| WO | 0051991 A1 | 9/2000 |
| WO | 0055141 A1 | 9/2000 |
| WO | 0078735 A1 | 12/2000 |
| WO | 0134574 A1 | 5/2001 |
| WO | 0168186 A2 | 9/2001 |
| WO | 0177104 A1 | 10/2001 |
| WO | 0218351 A1 | 3/2002 |
| WO | 0218372 A1 | 3/2002 |
| WO | 0218373 A1 | 3/2002 |
| WO | 0218375 A1 | 3/2002 |
| WO | 0218376 A1 | 3/2002 |
| WO | 0241882 A2 | 5/2002 |
| WO | 0250043 A1 | 6/2002 |
| WO | 03082290 A1 | 10/2003 |
| WO | 03089439 A1 | 10/2003 |
| WO | 03094921 A2 | 11/2003 |
| WO | 2004014426 A1 | 2/2004 |
| WO | 2004074263 A1 | 9/2004 |
| WO | 2004096224 A2 | 11/2004 |
| WO | 2004108664 A2 | 12/2004 |
| WO | 2005028470 A1 | 3/2005 |
| WO | 2005033096 A1 | 4/2005 |
| WO | 2005037824 A2 | 4/2005 |
| WO | 2005094357 A2 | 10/2005 |
| WO | 2006017317 A2 | 2/2006 |
| WO | 2006018182 A1 | 2/2006 |
| WO | 2006084058 A2 | 8/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147238 A1 | 12/2009 |
| WO | 2010081817 A1 | 7/2010 |
| WO | 2011003853 A2 | 1/2011 |
| WO | 2011069962 A1 | 6/2011 |

OTHER PUBLICATIONS

Bell, D.W. et al., "Inherited susceptibility to lung cancer may be associated with the T790M drug resistance mutation in EGFR". Nature Genetics, Dec. 2005, vol. 37, No. 12, p. 1315-1316. Published online Oct. 30, 2005.

Cancer Genome and Collaborative Group. Nature, Brief Communications Sep. 2004, vol. 431, p. 525-526.

Harari, P.M. "Epidermal growth factor receptor inhibition strategies in oncology". Endocrine-Related Cancer, 2004, vol. 11. p. 689-708.

Hirsh, V., "Afatinib (BIBW 2992) development in non-small-cell lung cancer". Future Oncol., 2011, 7(7), p. 817-825.

International Search Report and Written Opinion for PCT/EP2006/068313 mailed Feb. 26, 2007.

Johnson, J, et al. "Relationships between drug activity in NCI preclinical in vitro and in vitro and in vivo models and early clinical trials". British Journal of Cancer, 2001, 84 (10, p. 1424-1431.

Krozely, P. Abstract—Clinical Journal of Oncology Nursing, 2004, vol. 8, No. 2, p. 1092-1095.

Miller, V.A., et al., "Afatinib versus placebo for patients with advanced, metastatic non-small-cell lung cancer after failure of erlotinib, gefitinib, or both, and one or two lines of chemotherapy (LUX-Lung1): a phase 2b/3 randomised trial", The Lancet, Oncology, vol. 19, May 2012, pp. 528-538.

Paez, J. G. "EGFR Mutations in Lung Cancer: Correlation with Clinical Response to Gefitinib Therapy". Science, vol. 304, 2004, p. 1497-1500.

Sequist, L.V. et al., "1229PD / Lux-Lung 3: Symptom and Health-Related Quality of Life Results from a Randomized Phase III Study in 1st-Line Advanced NSCLC Patients Harbouring EGFR Mutations", Poster Discussion, Sep. 30, 2012 [downloaded from the internet Oct. 25, 2012. http://abstracts.webges.com/myitinerary/session-148.html?congress=esmo2012#.UFdGtBr1LSY.gmai].

Sequist, L.V., et al., "Neratinib, an Irrerversible Pan-ErbB Receptor Tyrosine Kinase Inhibitor: Results of a Phase II Trial in Patients with Advanced Non-Small-Cell Lung Cancer" Journal of Clinical Oncology, vol. 28, No. 18, Jun. 20, 2010, p. 3076-3083.

Subramaniam, D.S. et al., "BIBW 2992 in non-small cell lung cancer". Expert Opinion Investig. Drugs, 2011, 20(3), p. 415-422.

Vlahovic, G., et al., "Activation of Tyrosine Kinases in Cancer", The Oncologist, 2003, vol. 8, pp. 531-538.

Yanase, K. et al., "Gefitinib reverses breast cancer resistance protein-medicated drug resistance". Molecular Cancer Therapeutics, 2004, Vo. 9, No. 9, p. 1119-1125.

(56) References Cited

OTHER PUBLICATIONS

Yang, J. C-H, et al., "Afatinib for patients with lung adenocarcinoma and epidermal growth factor receptor mutations (LUX-Lung 2): a phase 2 trial", The Lancet, Oncology, vol. 13, May 2012, pp. 539-548.
Stedman's Medical Dictionary, 27th edition, Lippincott, Williams & Wilkins, Baltimore, 2000.
Subramaniam, D. S., et al., "BIBW 2992 in non-small cell lung cancer". Expert Opinion, Drug Evaluation, 2011, vol. 20, No. 3, p. 415-422.
Supplement ASCO Meeting Abstracts 1-4, Journal of Clinical Oncology, 2006.
Toyooka, S. et al., "EGFR Mutation and Response of Lung Cancer to Gefitinib." The New England Journal of Medicine, 2005, vol. 352, No. 20, p. 2136.
Tsou, Hwei-Ru, "6-Substituted-4-(3-bromophenylamino)quinazolines as Putative Irreversible Inhibitors of the Epidermal Growth Factor Receptor (EGFR) and Human Epidermal Growth Facotr Receptor (HER-2) Tyrosine Kinases with Enhanced Antitumore Activity", J. Med. Chem 2001, 2719-2734, vol. 44.
U.S. Appl. No. 12/914,003, filed Oct. 28, 2010, Inventor: Frank Himmelsbach.
Wikstrand, C. et al. "Monoclonal Antibodies against EGFRvIII Are Tumor Specific and React with Breast and Lung Carcinomas and Malignant Gliomas." Cancer Research, 1995, vol. 55, No. 14, pp. 3140-3148.
Wissner, A. et al., "Synthesis and Structure—Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)." Journal of Medicinal Chemistry, 2003, vol. 46, pp. 49-63.
Xu, Y. et al., "Acquired Resistance of Lung Adenocarcinoma to EGFR-tyrosine Kinase Inhibitors Gefitinib and Erlotinib." Cancer Biology & Therapy, 2010, vol. 9, No. 8, pp. 572-582.
Yanase, K. et al., "Gefitinib reverses breast cancer resistance protein-medicated drug resistance". Molecular Cancer Therapeutics, 2004, Vo. 9, No. 9, p. 119-1125.
Yoshimura, N. et al., "EKB-569, a new irreversible epidermal growth factor recptor tyrosine kinase inhibitor, with clinical activity in patients with non-small cell lung cancer with acquired resistance to gefitinib." Lung Cancer, 2006, vol. 51, pp. 363-368.
Abstract in English (2000) for DE19911366.
Abstract in English for WO199965228, 2010.
Agus, D.B. et al., Abstract: "A phase I dose escalation study of BIBW 2992, an irreversible dual EGFR/HER2 receptor tyrosine kinase inhibitor, in a continuous schedule in patients with advanced solid tumours." Journal of Clinical Oncology, 2006, ASCO Annual Meeting Proceedings (Post-Meeting Edition). vol. 24, No. 18S, (Jun. 20 Supplement), 2006, 2074.
Alan, R. "Benign Prostatic Hyperplasia (BPH)". Available at http://healthlibrary.epnet.com/GetContent/asp?token-1baaea3c-d4f5-4e14-8429-e3b3e1add7a7&chunkiid-1203, last reviewed Mar. 2006.
Argiris, A. et al., "Phase III Randomized, Placebo-Controlled Trial of Docetaxel With or Without Gefitinib in Recurrent or Metastatic Head and Neck Cancer: An Eastern Cooperative Oncology Group Trial." Journal of Clinical Oncology, 2013, vol. 31, No. 11, pp. 1405-1414.
Barton, J. et al., "Growth Factors and their Receptors: new Targets for Prostate Cancern Therapy". Urology 58 (Supplement 2A), Aug. 2001, p. 114-122.
Boehringer Ingelheim Press Release "Resistance to Epidermal Growth Factor Receptor (EGFR) Tyrosine Kinase Inhibitors (TKIs)." 2010.
Boehringer Ingelheim, "BIBW 2992: A Potent and Irreversible Inhibitor of EGFR/HER1 and HER2." Accessed on Jan. 3, 2012.
Boschelli, D., "4-Anilino-3-quinolinecarbonitriles: An Emerging Class of Kinase Inhibitors-An Update." Medicinal Chemistry Reviews—Online, 2004, vol. 1, pp. 457-463.

Burris, Ha et al.; "EGF1004: a randomized, multicenter, phase 1b study of the safety, biologic activity and clinical efficacy of the dual kinase inhibitor GW572016" Breast Cancer Research and Treatment, V. 82, suppl. 1 (2003), p. S18 #39.
Calabrisi, P. et al., Goodman * Gilman. "Section IX Chemotherapy of Neoplastic Diseases—Introduction". Goodman & Gilman's The Pharmacological Basis of Therapeutics, 10th ed, 2001, Hardman, JG, Limbird LE, Gilman AG, Eds. McGraw-Hill, NY, 2001, p. 1381-1388 (pp. 1381m 1383-1385 and 1388 provided).
Camp, E. et al., "Molecular Mechanisms of Resistance to Therapies Targeting the Epidermal Growth Factor Receptor." Clinical Cancer Research, 2005, vol. 11, No. 1, pp. 397-405.
Cancer Genome and Collaborative Group. Nature, Brief Communications, Sep. 2004, vol. 431, p. 525-526.
Chan, S.K. et al., "Mutations of the epidermal growth factor receptor in non-small cell lung cancer—Search and destroy." European Journal of Cancer 42, 2006, pp. 17-23.
Choong, N. et al., "Gefitinib Response of Erlotinib-refractory Lung Cancer Involving Meninges—Role of EGFR Mutation." Nature Clinical Practice Oncology, 2006, vol. 3, No. 1, pp. 50-57.
Chustecka, Zosia, "Afatinib Shows Modest Benefit in Head and Neck Cancer." Boehringer Ingelheim, European Society for Medical Oncology (ESMO) Congress 2014, Presented Sep. 27, 2014, Medscape.com.
deMiguel, M. et al., "Immunohistochemical comparative analysis of transforming grwoth factor a, epidermal growth factor, and epidermal growth factor receptor in normal, hyperplastic and neoplastic human prostates". Cytokine, 1998, p. 722-727.
Drug Data Report, "BIBW-2992" 2005, vol. 27, No. 11.
Duque, J.L. et al., "Heparin-Binding Epidermal Growth Factor-Like Growth Factor is an Autocrine Mediator of Human Prostate Stromal Cell Growth in Vitro". The Journal of Urology, vol. 165, Jan. 2001, p. 284-288.
European Society for Medical Oncology, "ESMO 2014 Press Release: Second-Line Afatinib Significantly Improves Progression-Free Survival in Recurrent or Metastatic Head and Neck Cancer, Phase III Trial Shows." Retrieved online Dec. 18, 2014. http://www.esmo.org/Conferences/ESMO-2014-Congress/Press-Media/Second-Line-Afatinib-Significantly-Innproves-Progression-Free-Survival-in-Recurrent-or-Metastatic-Head-and-Neck-Cancer-Phased-II-Trial-Shows.
European Society for Medical Oncology, "ESMO 2014: Afatinib vs Methotrexate in Second-Line Treatment of Recurrent and/or Metastatic Head and Neck Squamos Cell Carcinoma." Retrieved online Dec. 18, 2014. http://www.esmo.org/Conferences/ESMO-2014-Congress/News-Articles/Afatinib-vs-Methotrexate-in-Second-Line-Treatment-of-Recurrent-and-or-Metastatic-Head-and-Neck-Squamous-Cell-Carcinoma.
Fry, David W., "Inhibition of the Epidermal Growth Factor Receptor Family of Tyrosine Kinases as an Approach to Cancer Chemotherapy Progression from Reversible to Irreversible Inhibitors." Pharmacological & Therapeutics, 1999, vol. 82, No. 2-3, pp. 207-218.
Gonzales-Barcena, D. et al., "Responses to the antagonistic analog of LH-RH (SB-75, cetrorelix) in patients with benign prostatic hyperplasia and prostatic cancer". The Prostate, 1994, 24(2), p. 84-92, only abstract provided.
Goodman & Gilman's, "The Pharmacological Basis of Therapeutics" Tenth Edition, 2001, pp. 1381-1388.
Hansen, A.R. et al., "Epidermal Growth Factor Receptor Targeting in Head and Neck Cancer: Have We Been Just Skimming the Surface?" Journal of Clinical Oncology, 2013, vol. 31, No. 11, pp. 1381-1383.
Herbst, R.S. et al., "Monoclonal Antibodies to Target Epidermal Growth Factor Receptor-Positive Tumors". Cancer, Mar. 1, 2002, vol. 94, No. 5, p. 1593-1611.
Hirsh, V., "Afatinib (BIBW 2992) Development in Non-Small-Cell Lung Cancer." Future Oncology, 2011, vol. 7, pp. 817-825.
Hofmann, B .B., Chapter 10 Catecholamines, Sympathomimetic Drugs, and Adrenergic Receptor Antagonists. "Goodman and Gilman's the Pharmacological Basis of Therapeutics, 10th ed." Hardman JG, Limbird, LE, and Gilman AG, Eds. McGraw-Hill, 2001, p. 215-268, pp. 215, 247 and 248 provided).
International Search Report and Written Opinion for PCT/EP2007/059735 date mailed Dec. 6, 2007.

(56) References Cited

OTHER PUBLICATIONS

International Search Report and Written Opinion for PCT/EP2010/059546 mailed Nov. 22, 2011.

International Search Report for PCT/EP01/14569 mailed Mar. 1, 2002.

Kobayashi, S. et al.,"EGFR Mutation and Resistance of Non-Small-Cell Lung Cancer to Gefitinib." The New England Journal of Medicine, 2005, vol. 352, pp. 786-792.

Kwak, E. et al. "Irreversible Inhibitors of the EGF Receptor may Circumvent Acquired Resistance to Gefitinib." PNAS, 2005, vol. 102, No. 21, pp. 7665-7670.

Laird & Cherrington, "Small molecule tyrosine kinase inhibitors: clinical development of anticancer agents" Expert Opinion. Investig. Drugs.; Ashley Publications (2003) 12(1) p. 51-64.

Lee, M., "Tamsulosin for the Treatment of Benigh Prostatic Hypertrophy". The Annals of Pharmacotherapy, Feb. 2000, 34, p. 188-199.

Lewis, N., et al. Abstract: "A phase I dose escalation study of BIBW 2992, an irreversible dual EGFR/HER2 receptor tyrosine kinase inhibitor, in a 3 week on 1 week off schedule in patients with advanced solid tumors". Journal of Clinical Oncology, 2006 ASCO Annual Meeting Proceedings (Post-Meeting Edition). vol. 24, No. 18S (Jun. 20 Supplement), 2006: 3091.

Li, D. et al. "BIBW2992, An Irreversible EGFR/HER2 Inhibitor Highly Effective in Preclinical Lung Cancer Models." Oncogene, 2008, vol. 27, No. 34, pp. 4702-4711.

Martins, R.G. et al., "Cisplatin and Radiotherapy With or Without Erlotinib in Locally Advanced Squamous Cell Carcinoma of the Head and Neck: A Randomized Phase II Trial." Journal of Clinical Oncology, 2013, vol. 31, No. 11, pp. 1415-1421.

McMahon; VEGF Receptor Signaling in Tumor Angiogenesis; The Oncologist; 2000; 5 (suppl 1); pp. 3-10.

Mills; Humidity Control in Pharma Processing; Innovations in Pharmaceutical Technology; 2007; pp. 1-3.

Nosov et al., "Mekhanismy regulyatsii vnutrikletochnoi peredachi signala . . . " VIII Rossiskii Onkologicheskii Congress—Moscow, 2004.

Pinedo et al.; Translational Research: The Role of VEGF in Tumor Angiogenesis; The Oncologist; 2000; 5(suppl 1); pp. 1-2.

Plummer et al.; 573 POSTER Phase I study of BIBW2992, an oral irreversible dual EGFR/HER2 inhibitor, showing activity in tumors with mutated EGFR; European Journal of Cancer; Supplement; Nov. 2006; vol. 4; No. 12; Pergamon; Oxford, GB.

Rayford, W. et al., "Muscarinic Cholinergic Receptors Promote Growth of Human Prostate Cancer Cells". The Prostate, Feb. 1997, 30(3), p. 160-165.

Rosell, R. et al., "Crossing the Rubicon in Lung Adenocarcinoma: the Conundrum of EGFR Tyrosine Kinase Mutations." 2005, vol. 1, No. 3, pp. 319-322.

Sausville, E. A. et al. "Contributions of Human Tumor Xenografts to Anticancer Drug Development". Cancer Research, 2006, vol. 66 (7), p. 3351-3354.

Seiwert, T.Y. et al., "A randomized, phase II study of afatinib versus cetuximab in metastatic or recurrent squamous cell carcinoma of the head and neck." Annals of Oncology, 2014, vol. 25, No. 9, pp. 1813-1820.

Solca et al.; 567 POSTER Efficacy of BIBW 2992, an irreversible dual EGFR/HER2 receptor tyrosine kinase inhibitor, in combination with cytotoxic agents; European Journal of Cancer; Supplement; Nov. 2006; vol. 4; No. 12; Pergamon; Oxford, GB.

Solca, F. et al., "A242 BIBW 2992, an Irreversible Dual EGFR/HER2 Kinase Inhibitor, Shows Activity on L858R/T790M EGFR Mutants." and "A244 BIBW 2992, An Irreversible Dual EGFR/HER2 Receptor Tyrosine Kinase Inhibitor for Cancer Therapy." Molecular Targets and Cancer Therapeutics, Nov. 2005.

--Figure 1: BIBW 2992 induces apoptosis in NCI-N87 gastric cancer cells

Figure 2: Effect of BIBW 2992 on the growth of preexisting HNSCC FaDu xenografts

Figure 3: Effect of BIBW 2992 on the growth of MDA-MB-453 and SKOV-3 xenografts

Figure 4: Effect of BIBW 2992 on the growth of MDA-MB-453 and SKOV-3 xenografts

QUINAZOLINE DERIVATIVES FOR THE TREATMENT OF CANCER DISEASES

The present invention relates to the use of quinazolines of formula (I), wherein the groups $R^a$ to $R^d$ have the meanings given in the claims and specification, in cancer therapy.

BACKGROUND OF THE INVENTION

Compounds of formula (I) are disclosed in WO 02/50043, WO 2004/074263 and WO 2005/037824 as dual inhibitors of erbb1 receptor (EGFR) and erbB2 (Her2/neu) receptor tyrosine kinases, suitable for the treatment of e.g. benign or malignant tumours, particularly tumours of epithelial and neuroepithelial origin, metastasisation and the abnormal proliferation of vascular endothelial cells (neoangiogenesis), for treating diseases of the airways and lungs which are accompanied by increased or altered production of mucus caused by stimulation by tyrosine kinases, as well as for treating diseases of the gastrointestinal tract and bile duct and gall bladder which are associated with disrupted activity of the tyrosine kinases. The disclosure of WO 02/50043, WO 2004/074263 and WO 2005/037824 includes preparation as well as pharmaceutical formulations of the compounds and is incorporated by reference regarding these aspects. Furthermore, it is known for treatment of tumour diseases that the compounds may be used in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons) or antibodies.

SUMMARY OF THE INVENTION

It has been found that the compounds of formula (I) provide unexpected advantages in the treatment of cancer, e.g. superior efficacy and/or reduced side effects, especially in the treatment of several specific cancer-subindications.

A first aspect of the present invention therefore is a method of treating cancer, preferably the specific cancer-subindications referred to hereinafter, said method comprising administering a therapeutically effective amount of a compound of formula (I) to a patient in need thereof, optionally in combination with radiotherapy, radio-immunotherapy and/or tumour resection by surgery.

Any reference to a compound of formula (I) in connection with the invention should be understood to include the tautomers, racemates, enantiomers and diastereomers thereof, if any, the mixtures thereof as well as the pharmacologically acceptable acid addition salts, solvates, hydrates, polymorphs, physiologically functional derivatives or prodrugs thereof.

The expression "patient" relates to a human or non-human mammalian patient suffering from cancer and thus in need of such treatment, preferably the patient is a human person. Furthermore, the expression "patient" should be understood to include such cancer patients carrying tumors with wild-type EGF receptor as well as pre-selected cancer patients with tumors harboring activating EGFR mutations. These can be located in the tyrosine kinase domain of the EGF receptor such as for instance the L858R or L861 point mutations in the activation loop (exon 21), or in-frame deletion/insertion mutations in the ELREA sequence (exon 19), or substitutions in G719 situated in the nucleotide binding loop (exon 18). Additional activating mutations have been reported in the extracellular domain of the EGF receptor in various indications (e.g. EGFR vIII displaying exon 2-7 deletions). Other mutations such as the T790M point mutation in exon 20 as well as certain exon 20 insertions (e.g. D770_N771insNPG) which confer resistance to particular drugs should also be included, as well as double mutants such as the combined L858R/T790M mutation or the exon-19-del/T790M.

The expression "patient" should be understood to include also such cancer patients carrying tumors with wild-type HER2 receptor as well as pre-selected cancer patients with tumors harboring activating HER2 mutations, e.g. M774_A775insAYVM.

The indication "cancer" as used in the context of the invention is to be understood in a most general sense as a disease characterized by inappropriate cellular proliferation, migration, apoptosis or angiogenesis, preferably by inappropriate cellular proliferation. Inappropriate cell proliferation means cellular proliferation resulting from inappropriate cell growth, from excessive cell division, from cell division at an accelerated rate and/or from inappropriate cell survival.

"Radiotherapy" means administering ionizing radiation to the patient, as conventionally used in cancer therapy. Radiotherapy may be applied before, in parallel or after treatment by administration of a compound of formula (I).

"Tumour resection by surgery" is one standard option in cancer therapy and may be applied before or after treatment by administration of a compound of formula (I).

A second aspect of the present invention is directed to the use of a compound of formula (I) for the manufacture of a medicament for the treatment of cancer, preferably for the treatment of the specific cancer-subindications referred to hereinafter.

DETAILED DESCRIPTION OF THE INVENTION

In a first embodiment (1), both with regard to the first and second aspect of the invention, formula (I)

(I)

is defined to encompass those compounds wherein
$R^a$ denotes a benzyl, 1-phenylethyl or 3-chloro-4-fluorophenyl group,
$R^b$ denotes a hydrogen atom or a $C_{1-4}$-alkyl group,
$R^c$ denotes a cyclopropylmethoxy, cyclobutyloxy, cyclopentyloxy, tetrahydrofuran-3-yl-oxy, tetrahydrofuran-2-yl-methoxy, tetrahydrofuran-3-yl-methoxy, tetrahydropyran-4-yl-oxy or tetrahydropyran-4-yl-methoxy group,
$R^d$ denotes a dimethylamino, N-cyclopropyl-N-methyl-amino, N-cyclopropylmethyl-N-methyl-amino, N-ethyl-N-methyl-amino, N,N-diethylamino, N-isopropyl-N-methyl-amino, N-(2-methoxyethyl)-N-methyl-amino, N-(1-methoxy-2-propyl)-N-methyl-amino, N-(3-methoxypropyl)-N-methyl-amino, pyrrolidino, 2-methylpyrrolidino, 2-(methoxymethyl)-pyrrolidino, morpholino, (1S,4S)-2-oxa-5-aza-bicyclo[2.2.1]hept-5-yl, (1R,4R)-2-oxa-5-aza-bicyclo[2.2.1]hept-5-yl, N-cyclopropyl-N-methyl-amino-, N-methyl-N-(tetrahydrofuran-3-yl)-amino, N-methyl-N-(tetrahydrofuran-2-ylmethyl)-amino, N-methyl-N-(tetrahydrofuran-3-yl-methyl)-amino, N-methyl-N(tetrahydropyran-4-yl)-amino or N-methyl-N-(tetrahydropyran-4-yl-methyl)-amino group, or a group of formula (II)

(III)

wherein $R^e$ and $R^f$, which may be identical or different, in each case denote a hydrogen atom or a $C_{1-3}$-alkyl group, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof.

In a second embodiment (2), both with regard to the first and second aspect of the invention, formula (I)

(I)

is defined to encompass those compounds wherein
$R^a$ denotes a 3-chloro-4-fluorophenyl group,
$R^b$ denotes a hydrogen atom,
$R^c$ denotes a cyclopropylmethoxy, cyclobutyloxy, cyclopentyloxy, tetrahydrofuran-3-yl-oxy, tetrahydrofuran-2-yl-methoxy, tetrahydrofuran-3-yl-methoxy, tetrahydropyran-4-yl-oxy or tetrahydropyran-4-yl-methoxy group,
$R^d$ denotes a dimethylamino, N-cyclopropyl-N-methyl-amino, N-cyclopropylmethyl-N-methyl-amino, N-ethyl-N-methyl-amino, N,N-diethylamino, N-isopropyl-N-methyl-amino, N-(2-methoxyethyl)-N-methyl-amino, N-(1-methoxy-2-propyl)-N-methyl-amino, N-(3-methoxypropyl)-N-methyl-amino, pyrrolidino, 2-methylpyrrolidino, 2-(methoxymethyl)-pyrrolidino, morpholino, (1S,4S)-2-oxa-5-aza-bicyclo[2.2.1]hept-5-yl, (1R,4R)-2-oxa-5-aza-bicyclo[2.2.1]hept-5-yl, N-methyl-N-(tetrahydrofuran-3-yl)-amino, N-methyl-N-(tetrahydrofuran-2-yl-methyl)-amino, N-methyl-N-(tetrahydrofuran-3-yl-methyl)-amino, N-methyl-N-(tetrahydropyran-4-yl)-amino or N-methyl-N-(tetrahydropyran-4-yl-methyl)-amino group, or a group of formula (II)

(III)

wherein $R^e$ and $R^f$ denote a hydrogen atom.

In a third embodiment (3), both with regard to the first and second aspect of the invention, formula (I)

(I)

is defined to encompass those compounds wherein
$R^a$ denotes a 3-chloro-4-fluorophenyl group,
$R^b$ denotes a hydrogen atom,
$R^c$ denotes a tetrahydrofuran-3-yl-oxy, tetrahydrofuran-2-yl-methoxy, tetrahydrofuran-3-yl-methoxy, tetrahydropyran-4-yl-oxy or tetrahydropyran-4-yl-methoxy group,
$R^d$ denotes a dimethylamino, N-cyclopropyl-N-methyl, N-ethyl-N-methyl-amino, N,N-diethylamino, N-isopropyl-N-methyl-amino, morpholino, (1S,4S)-2-oxa-5-aza-bicyclo-[2.2.1]hept-5-yl or (1R,4R)-2-oxa-5-aza-bicyclo[2.2.1]hept-5-yl, group, or a group of formula (II)

(III)

wherein $R^e$ and $R^f$ denote a hydrogen atom.

In a fourth embodiment (4), both with regard to the first and second aspect of the invention, formula (I)

is defined to encompass those compounds wherein
$R^a$ denotes a 3-chloro-4-fluorophenyl group,
$R^b$ denotes a hydrogen atom,
$R^c$ denotes a tetrahydrofuran-3-yl-oxy, tetrahydrofuran-2-yl-methoxy or tetrahydrofuran-3-yl-methoxy group,
$R^d$ denotes a dimethylamino group or a group of formula (II)

wherein $R^e$ and $R^f$, denote a hydrogen atom.

In a fifth embodiment (5), both with regard to the first and second aspect of the invention, formula (I) is defined to encompass the compounds selected from the group consisting of (a) 4-[(3-chloro-4-fluorophenyl)amino]-6-{[4-(N,N-dimethylamino)-1-oxo-2-buten-1-yl]amino}-7-cyclobutyloxy-quinazoline,
(b) 4-[(3-chloro-4-fluorophenyl)amino]-6-{[4-(N,N-dimethylamino)-1-oxo-2-buten-1-yl]amino}-7-cyclopentyloxy-quinazoline,
(c) 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline,
(d) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,
(e) 4-[(3-chloro-4-fluorophenyl)amino]-6-{[4-(N,N-dimethylamino)-1-oxo-2-buten-1-yl]amino}-7-(tetrahydropyran-4-yloxy)-quinazoline,
(f) 4-[(3-chloro-4-fluorophenyl)amino]-6-{[4-(N,N-dimethylamino)-1-oxo-2-buten-1-yl]amino}-7-[(tetrahydrofuran-2-yl)-methoxy]-quinazoline,
(g) 4-[(3-chloro-4-fluorophenyl)amino]-6-{[4-(N,N-dimethylamino)-1-oxo-2-buten-1-yl]amino}-7-[(tetrahydrofuran-3-yl)-methoxy]-quinazoline,
(h) 4-[(R)-(1-phenyl-ethyl)amino]-6-{[4-(N,N-dimethylamino)-1-oxo-2-buten-1-yl]amino}-7-cyclopropylmethoxy-quinazoline,
(i) 4-[(3-chloro-4-fluorophenyl)amino]-6-{[4-(morpholin-4-yl)-1-oxo-2-buten-1-yl]amino}-7-[tetrahydrofuran-2-yl)methoxy]-quinazoline,
(j) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline,
(k) 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline,
(l) 4-[(3-chloro-4-fluoro-phenyl)amino]-6-{[4-(N-ethyl-N-methyl-amino)-1-oxo-2-buten-1-yl]amino}-7-[(S)-(tetrahydrofuran-3-yl)oxy]-quinazoline,
(m) 4-[(3-chloro-4-fluoro-phenyl)amino]-6-{[4-(N-isopropyl-N-methyl-amino)-1-oxo-2-buten-1-yl]amino}-7-[(S)-(tetrahydrofuran-3-yl)oxy]-quinazoline,
(n) 4-[(3-chloro-4-fluoro-phenyl)amino]-6-{[4-(N-cyclopropyl-N-methyl-amino)-1-oxo-2-buten-1-yl]amino}-7-cyclopentyloxy-quinazoline,
(o) 4-[(3-chloro-4-fluoro-phenyl)amino]-6-{[4-(N,N-diethyl-amino)-1-oxo-2-buten-1-yl]amino}-7-cyclopropylmethoxy-quinazoline,
(p) 4-[(3-chloro-4-fluoro-phenyl)amino]-6-{[4-((1S,4S)-2-oxa-5-aza-bicyclo[2.2.1]-hept-5-yl)-1-oxo-2-buten-1-yl]amino}-7-[(S)-(tetrahydrofuran-3-yl)oxy]-quinazoline,
(q) 4-[(3-chloro-4-fluoro-phenyl)amino]-6-{[4-((1R,4R)-2-oxa-5-aza-bicyclo[2.2.1]-hept-5-yl)-1-oxo-2-buten-1-yl]amino}-7-[(S)-(tetrahydrofuran-3-yl)oxy]-quinazoline and
(r) 4-[(3-chloro-4-fluoro-phenyl)amino]-6-{[4-(dimethylamino)-1-oxo-2-buten-1-yl]amino}-7-cyclopropylmethoxy-quinazoline.

In a sixth embodiment (6), both with regard to the first and second aspect of the invention, the compounds of formula (I) are selected from the group consisting of (d) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (k) 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, the dimaleate salt of compound (d) being especially preferred:

(d') 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate.

In a preferred embodiment the invention relates to the use of a compound of formula (I) according to the invention, wherein the disease is cancer selected from the group consisting of carcinomas, sarcomas, melanomas, myelomas, hematological neoplasias, lymphomas and childhood cancers.

Examples of carcinomas within the scope of the invention include but are not limited to adenocarcinoma (AC), squamous cell carcinoma (SCC) and mixed or undifferentiated carcinomas. Carcinomas within the scope of the invention include but are not limited to the following histologies:

Head and neck tumours: SCC, AC, transitional cell cancers, mucoepidermoid cancers, undifferentiated carcinomas;

Central nervous system tumours: Astrocytoma, glioblastoma, meningeoma, neurinoma, schwannoma, ependymoma, hypophysoma, oligodendroglioma, medulloblastoma;

Bronchial and mediastinal tumours:
  Bronchial tumours:
    Small cell lung cancers (SCLC): oat-cell lung cancer, intermediate cell cancer, combined oat-cell lung cancer;
    Non-small cell lung cancers (NSCLC): SCC, spindle cell carcinoma, AC, bronchioalveolar carcinoma, large cell NSCLC, clear cell NSCLC;
  Mesothelioma;
  Thymoma;
  Thyroid carcinomas: papillary, follicular, anaplastic, medullary;
Tumours of the gastrointestinal tract:
  Oesophageal cancers: SCC, AC, anaplastic, carcinoid, sarcoma;
  Gastric cancers: AC, adenosquamous, anaplastic;
  Colorectal cancers: AC, including hereditary forms of AC, carcinoid, sarcoma;
  Anal cancers: SCC, transitional epithelial cancer, AC, basal cell carcinoma;
  Pancreatic cancers: AC, including ductal and acinary cancers, papillary, adenosquamous, undifferentiated, tumours of the endocrine pancreas;
  Hepatocellular carcinoma, cholangiocarcinoma, angiosarcoma, hepatoblastoma;
  Biliary carcinomas: AC, SCC, small cell, undifferentiated;
  Gastrointestinal stroma tumours (GIST);
Gynaecological cancers:
  Breast cancers: AC, including invasive ductal, lobular and medullary cancers, tubular, mucinous cancers, Paget-carcinoma, inflammatory carcinoma, ductal and lobular carcinoma in situ;
  Ovarian cancers: Epithelial tumours, stroma tumours, germ cell tumours, undifferentiated tumours;
  Cervical cancers: SCC, AC, mixed and undifferentiated tumours;
  Endometrial cancers: AC, SCC, mixed, undifferentiated tumours;
  Vulvar cancers: SCC, AC;
  Vaginal cancers: SCC, AC;
Urinary tract and testicular cancers:
  Testicular cancers: seminoma;
  Non-seminomatous germ cell tumours: teratoma, embryonal cell carcinoma, choriocarcinoma, yolk sac tumour, mixed, Sertoli and Leydig-cell tumours;
  Extragonadal germ cell tumours;
  Prostate cancers: AC, small cell, SCC;
  Renal cell cancers: AC, including clear cell, papillary and chromophobous carcinomas, hereditary forms (e.g. von-Hippel-Lindau syndrome), nephroblastoma;
  Urinary bladder cancers: transitional cell (urothelial) cancers, SCC, AC;
  Urethral cancers: SCC, transitional cell cancers, AC;
  Penile cancers: SCC;
Tumours of endocrine tissue:
  Thyroid cancers: papillary, follicular, anaplastic, medullary carcinomas, including MEN syndrome;
  Tumours of the endocrine pancreas;
  Carcinoids;
  Pheochromocytoma.

Examples of sarcomas within the scope of the invention include but are not limited to Ewing-sarcoma, osteosarcoma or osteogenic sarcoma, chondrosarcoma, synovial sarcoma, leiomyosarcoma, rhabdomyosarcoma, mesothelial sarcoma or mesothelioma, fibrosarcoma, angiosarcoma or hemangioendothelioma, liposarcoma, glioma or astrocytoma, myxosarcoma, malignant fibrous histiocytoma, mesenchymous or mixed mesodermal tumour, neuroblastoma and clear cell sarcoma.

Examples of melanomas within the scope of the invention include but are not limited to superficial spreading melanoma, nodular and lentigo-maligna melanoma.

Examples of myelomas within the scope of the invention include but are not limited to immunocytoma, plasmocytoma and multiple myeloma.

In another preferred embodiment the invention relates to the use according to the invention, wherein the hematological neoplasia is leukemia.

Further examples of hematologic neoplasias within the scope of the invention include but are not limited to acute or chronic leukemias of myeloid, erythroid or lymphatic origin, myelodysplastic syndromes (MDS) and myeloproliferative syndromes (MPS, such as chronic myelogeneous leukemia, osteomyelofibrosis, polycythemia vera or essential thrombocythemia).

Examples of lymphomas within the scope of the invention include but are not limited to:
  Hodgkin's-lymphoma;
  Non-Hodgkin's-lymphomas: T- and B-cell lymphomas
    B-cell lymphomas:
      Low and intermediate grade: Chronic lymphocytic leukemia (CLL), prolymphocytic leukemia (PLL), small lymphocytic lymphoma, hairy cell leukemia, plasmacytoid lymphoma, mantle cell lymphoma, follicular lymphoma, marginal zone lymphoma including MALT-lymphoma;
      High grade: diffuse large B-cell lymphoma (DLBCL including immunoblastic and centroblastic variants), lymphoblastic, Burkitt's lymphoma;
    T-cell lymphomas:
      Low grade: T-CLL, T-PLL, Mycosis fungoides, Sezary-syndrome;
      High grade: Anaplastic large cell, T-immunoblastic and lymphoblastic.

In another preferred embodiment the invention relates to the use according to the invention, wherein the disease is cancer selected from the group consisting of mixed tumours, undifferentiated tumours and metastases thereof.

Examples of mixed tumours within the scope of the invention include but are not limited to adenosquamous carcinomas, mixed mesodermal tumours, carcinosarcomas and teratocarcinomas.

Examples of undifferentiated, other tumours or metastases thereof within the scope of the invention include but are not limited to undifferentiated tumours, carcinomas of unknown primary (CUP), metastases of unknown primary (MUP) and pheochromocytoma, carcinoids.

Additionally the following tumour diseases which can be treated with a compound of formula (I) in accordance with the invention are summarized:
acral lentiginous melanoma, actinic keratoses, adenoid cycstic carcinoma, adenomas, adenosarcoma, adrenocortical carcinoma, AIDS-related lymphoma, bartholin gland carcinoma, brain stem glioma, capillary carcinoma, central nervous system lymphoma, chondosarcoma, choriod plexus papilloma/carcinoma, cystadenoma, endodermal sinus tumor, endometrial hyperplasia, endometrial stromal sarcoma, endometrioid adenocarcinoma, epitheloid, focal nodular hyperplasia, gastrinoma, gestational trophoblastic tumor, glucagonoma, hepatic adenoma, hepatic adenomatosis, hypopharyngeal cancer, hypothalamic and visual pathway glioma, insulinoma, intraepithelial neoplasia, interepithelial squamous cell neoplasia, intraocular invasive squamous cell carcinoma, large cell carcinoma, islet cell carcinoma, Kaposi's sarcoma, laryngeal cancer, leukemia-related disorders, lip and oral cavity cancer, malignant mesothelial tumors, malignant thymoma, medulloepithelioma, merkel cell carcinoma, mucoepidermoid carcinoma, multiple myeloma/plasma cell neoplasm, mycosis fungoides, myelodysplastic syndrome, myeloproliferative disorders, nasal cavity and paranasal sinus cancer, nasopharyngeal cancer, neuroepithelial adenocarcinoma, nodular melanoma, oat cell carcinoma, oligodendroglial, oral cancer, oropharyngeal cancer, pineal cell, pituitary tumors, pseudosarcoma, pulmonary blastoma, parathyroid cancer, pineal and supratentorial primitive neuroectodermal tumors, pituitary tumor, plasma cell neoplasm, pleuropulmonary blastoma, retinoblastoma, serous carcinoma, small intestine cancer, soft tissue carcinomas, somatostatin-secreting tumor, supratentorial primitive neuroectodermal tumors, uveal melanoma, verrucous carcinoma, vipoma, Waldenstrom's macroglobulinemia, well differentiated carcinoma, and Wilm's tumor.

In a further preferred embodiment (7), both with regard to the first and second aspect of the invention, the compounds of formula (I) are selected from the group consisting of
(a) 4-[(3-chloro-4-fluorophenyl)amino]-6-{[4-(N,N-dimethylamino)-1-oxo-2-buten-1-yl]amino}-7-cyclobutyloxy-quinazoline,
(b) 4-[(3-chloro-4-fluorophenyl)amino]-6-{[4-(N,N-dimethylamino)-1-oxo-2-buten-1-yl]amino}-7-cyclopentyloxy-quinazoline,
(c) 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline,
(d) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline (BIBW2992),
(e) 4-[(3-chloro-4-fluorophenyl)amino]-6-{[4-(N,N-dimethylamino)-1-oxo-2-buten-1-yl]amino}-7-(tetrahydropyran-4-yloxy)-quinazoline,
(f) 4-[(3-chloro-4-fluorophenyl)amino]-6-{[4-(N,N-dimethylamino)-1-oxo-2-buten-1-yl]amino}-7-[(tetrahydrofuran-2-yl)-methoxy]-quinazoline,
(g) 4-[(3-chloro-4-fluorophenyl)amino]-6-{[4-(N,N-dimethylamino)-1-oxo-2-buten-1-yl]amino}-7-[(tetrahydrofuran-3-yl)-methoxy]-quinazoline,
(h) 4-[(R)-(1-phenyl-ethyl)amino]-6-{[4-(N,N-dimethylamino)-1-oxo-2-buten-1-yl]amino}-7-cyclopropylmethoxy-quinazoline,
(i) 4-[(3-chloro-4-fluorophenyl)amino]-6-{[4-(morpholin-4-yl)-1-oxo-2-buten-1-yl]amino}-7-[(tetrahydrofuran-2-yl)-methoxy]-quinazoline,
(j) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline,
(k) 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, and
(r) 4-[(3-chloro-4-fluoro-phenyl)amino]-6-{[4-(dimethylamino)-1-oxo-2-buten-1-yl]amino}-7-cyclopropylmethoxy-quinazoline,
and the cancer indication to be treated by administration of a compound of formula (I) is selected from the group consisting of
Head and neck tumours: SCC, AC, transitional cell cancers, mucoepidermoid cancers, undifferentiated carcinomas;
Central nervous system tumours: Astrocytoma, glioblastoma, meningeoma, neurinoma, schwannoma, ependymoma, hypophysoma, oligodendroglioma, medulloblastoma;
Bronchial and mediastinal tumours:
Bronchial tumours:
Non-small cell lung cancers (NSCLC): SCC, spindle cell carcinoma, AC, bronchioalveolar carcinoma, large cell NSCLC, clear cell NSCLC;
Thyroid carcinomas: papillary, follicular, anaplastic, medullary;
Tumours of the gastrointestinal tract:
Oesophageal cancers: SCC, AC, anaplastic;
Gastric cancers: AC, adenosquamous, anaplastic;
Colorectal cancers: AC, including hereditary forms of AC, carcinoid, sarcoma;
Pancreatic cancers: AC, including ductal and acinary cancers, papillary, adenosquamous, undifferentiated, tumours of the endocrine pancreas;
Hepatocellular cancers, cholangiocarcinoma
Gynaecological cancers:
Breast cancers: AC, including invasive ductal, lobular and medullary cancers, tubular, mucinous cancers, Paget-carcinoma, inflammatory carcinoma, ductal and lobular carcinoma in situ;
Ovarian cancers: Epithelial tumours, stroma tumours, germ cell tumours, undifferentiated tumours;
Urinary tract and testicular cancers:
Prostate cancers: AC, small cell, SCC;
Renal cell cancers: AC, including clear cell, papillary and chromophobous carcinomas, hereditary forms (e.g. von-Hippel-Lindau syndrome), Wilm's tumor, nephroblastoma;
Urinary bladder cancers: transitional cell (urothelial) cancers, SCC, AC.

Examples of sarcomas within the scope of the invention include but are not limited to Ewing-sarcoma, osteosarcoma or osteogenic sarcoma, chondrosarcoma, synovial sarcoma, leiomyosarcoma, rhabdomyosarcoma, mesothelial sarcoma or mesothelioma, fibrosarcoma, angiosarcoma or hemangioendothelioma, liposarcoma, glioma or astrocytoma, myxosarcoma, malignant fibrous histiocytoma, mesenchymous or mixed mesodermal tumour, neuroblastoma and clear cell sarcoma.

In a very preferred embodiment (8), both with regard to the first and second aspect of the invention, the compounds of formula (I) are selected from the group consisting of
(d) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline (BIBW2992),
(k) 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline,
the dimaleate salt of compound (d) being especially preferred:
(d') 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate (BIBW2992 MA$_2$),
and the cancer indication to be treated by administration of a compound of formula (I) is selected from the group consisting of
Head and neck tumours: SCC, AC, transitional cell cancers, mucoepidermoid cancers, undifferentiated carcinomas;
Colorectal cancers, metastatic or non-metastatic: AC, including hereditary forms of AC, carcinoid, sarcoma;

Pancreatic cancers: AC, including ductal and acinary cancers, papillary, adenosquamous, undifferentiated, tumours of the endocrine pancreas;

Breast cancers, metastatic or non-metastatic: AC, including invasive ductal, lobular and medullary cancers, tubular, mucinous cancers, Paget-carcinoma, inflammatory carcinoma, ductal and lobular carcinoma in situ;

Prostate cancers: AC, small cell, SCC;

Gastric cancers: AC, adenosquamous, anaplastic;

Ovarian cancer;

Non-small cell lung cancers (NSCLC): SCC, spindle cell carcinoma, AC, bronchioalveolar carcinoma, large cell NSCLC, clear cell NSCLC.

It is known that cancer patients carrying activating EGFR mutations in their tumors, i.e. within the tyrosine kinase domain of the EGF receptor, may show increased sensitivity to treatment with EGFR inhibitors. Analogously, cancer patients carrying activating HER2 mutations, e.g. M774_A775insAYVM, in their tumors may show increased sensitivity to treatment with HER2 inhibitors. Both groups of patients as well as a subgroup carrying both activating EGFR and HER2 mutations may show increased sensitivity to treatment with dual inhibitors of erbb1 receptor (EGFR) and erbB2 (Her2/neu).

The presence of specific gain-of-function mutations within the tyrosine kinase domain of the EGF receptor in a subgroup of NSCLC patients has been associated with increased sensitivity to treatment with gefitinib and erlotinib (Lynch, New England Journal Medicine 350, 2129 (2004); Paez, Science 304, 1497 (2004); Pao, Proceedings of the National Academy of Science of the United States 101, 13306 (2004)). In particular, the L858R point mutation (exon 21) as well as deletion/insertion mutations in the ELREA sequence (exon 19) account for the majority of gefitinib responders. A secondary point mutation in exon 20, T790M, is associated with acquired resistance to gefitinib or erlotinib. This mutation is analogous to the T315I mutation identified in CML patients who relapse under imatinib treatment (imatinib resistant patients).

Irreversible inhibitors (e.g., HKI-272 or CL 387,785), in contrast to reversible inhibitors (e.g., gefitinib), are able to inhibit proliferation and EGF-induced EGFR phosphorylation in cell lines expressing double mutant EGF receptors (Kwak, Proceedings of the National Academy of Science of the United States 102, 7665 (2005) and Kobayashi, New England Journal Medicine 352, 786 (2005)).

Any aspect of the present invention therefore includes, as a sub-aspect, optional pre-selection of cancer patients for an EGFR mutation in the tyrosine kinase domain of the EGF receptor as well as pre-selection of cancer patients for an HER2 mutation. The EGFR mutations preferably relevant in in this context are selected from the group consisting of the L858R and L861 point mutations in the activation loop (exon 21), in-frame deletion/insertion mutations in the ELREA sequence (exon 19), substitutions in G719 situated in the nucleotide binding loop (exon 18), activating mutations in the extracellular domain of the EGF receptor such as EGFR vIII displaying exon 2-7 deletions, the T790M point mutation in exon 20, exon 20 insertions such as D770_N771insNPG, and double mutants such as the combined L858R/T790M mutation and the exon-19-del/T790M. The HER2 mutation preferably relevant in in this context is the M774_A775insAYVM mutation.

Methods for detecting mutations in the tyrosine kinase domain of the EGF receptor are known in the art, several corresponding diagnostic tools are approved by the FDA and commercially available, e.g. an assay for the detection of epidermal growth factor receptor mutations in patients with non-small cell lung cancer (Genzyme Corp.; see also Journal of Clinical Oncology, 2006 ASCO Annual Meeting Proceedings (Post-Meeting Edition). Vol 24, No 18S (June 20 Supplement), 2006: Abstract 10060).

Any of the embodiments of the invention mentioned hereinbefore defining compounds of formula (I) and cancer indications applies accordingly to the optional sub-aspect of pre-selection of cancer patients for an activating EGFR mutation in the tyrosine kinase domain of the EGF receptor and/or pre-selection of cancer patients for an activating HER2 mutation. Treatment of EGFR mutant cancer patients with the compounds of formula (I) may allow a response in cancer patients with acquired or persistent resistance to gefitinib or erlotinib treatment. Treatment of cancer patients carrying an activating HER2 mutant in their tumors with the compounds of formula (I) may allow a response in cancer patients with acquired or persistent resistance to certain chemotherapeutics such as e.g. lapatinib or herceptin.

Most preferred cancer indications with EGFR or HER2 mutations relevant in connection with the sub-aspect of patient pre-selection for mutations are selected from the group consisting of Head and neck tumours: SCC, AC, transitional cell cancers, mucoepidermoid cancers, undifferentiated carcinomas;

Colorectal cancers, metastatic or non-metastatic: AC, including hereditary forms of AC, carcinoid, sarcoma;

Pancreatic cancers: AC, including ductal and acinary cancers, papillary, adenosquamous, undifferentiated, tumours of the endocrine pancreas;

Breast cancers, metastatic or non-metastatic: AC, including invasive ductal, lobular and medullary cancers, tubular, mucinous cancers, Paget-carcinoma, inflammatory carcinoma, ductal and lobular carcinoma in situ;

Prostate cancers: AC, small cell, SCC;

Gastric cancers: AC, adenosquamous, anaplastic;

Ovarian cancer;

Non-small cell lung cancers (NSCLC): SCC, spindle cell carcinoma, AC, bronchioalveolar carcinoma, large cell NSCLC, clear cell NSCLC, but especially Non-small cell lung cancers (NSCLC): SCC, spindle cell carcinoma, AC, bronchioalveolar carcinoma, large cell NSCLC, clear cell NSCLC, especially metastatic, second line patients who have failed at least one prior chemotherapy regimen or 3rd/4th line patients who have received Tarceva or Iressa for at least 12 weeks and then failed, preferably to be treated by administration of a compound of formula (I) selected from the group consisting of:

(a) 4-[(3-chloro-4-fluorophenyl)amino]-6-{[4-(N,N-dimethylamino)-1-oxo-2-buten-1-yl]amino}-7-cyclobutyloxy-quinazoline, (b) 4-[(3-chloro-4-fluorophenyl)amino]-6-{[4-(N,N-dimethylamino)-1-oxo-2-buten-1-yl]amino}-7-cyclopentyloxy-quinazoline, (c) 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, (d) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline (BIBW2992), (e) 4-[(3-chloro-4-fluorophenyl)amino]-6-{[4-(N,N-dimethylamino)-1-oxo-2-buten-1-yl]amino}-7-(tetrahydropyran-4-yloxy)-quinazoline, (f) 4-[(3-chloro-4-fluorophenyl)amino]-6-{[4-(N,N-dimethylamino)-1-oxo-2-buten-1-yl]amino}-7-[(tetrahydrofuran-2-yl)-methoxy]-quinazoline,
(g) 4-[(3-chloro-4-fluorophenyl)amino]-6-{[4-(N,N-dimethylamino)-1-oxo-2-buten-1-yl]amino}-7-[(tetrahydrofuran-3-yl)-methoxy]-quinazoline,
(h) 4-[(R)-(1-phenyl-ethyl)amino]-6-{[4-(N,N-dimethylamino)-1-oxo-2-buten-1-yl]amino}-7-cyclopropylmethoxy-quinazoline,
(i) 4-[(3-chloro-4-fluorophenyl)amino]-6-{[4-(morpholin-4-yl)-1-oxo-2-buten-1-yl]amino}-7-[(tetrahydrofuran-2-yl)-methoxy]-quinazoline,
(j) 4-[(3-chloro-4-fluorophenyl)amino]-6-{[4-(N,N-dimethylamino)-1-oxo-2-buten-1-yl]amino}-7-[(S)-(tetrahydrofuran-2-yl)-methoxy]-quinazoline,
(k) 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, and
(r) 4-[(3-chloro-4-fluoro-phenyl)amino]-6-{[4-(dimethylamino)-1-oxo-2-buten-1-yl]amino}-7-cyclopropylmethoxy-quinazoline, or a pharmaceutically acceptable salt thereof.

The first aspect of the present invention therefore includes, as a sub-aspect (A), a method of treating cancer comprising pre-selection of cancer patients for EGFR and/or HER2 mutations and administering a therapeutically effective amount of a compound of formula (I) to a pre-selected cancer patient shown to carry an EGFR mutation in the tyrosine kinase domain of the EGF receptor and/or with a tumor harboring an activating HER2 mutation, optionally in combination with radiotherapy, radio-immunotherapy and/or tumour resection by surgery.

Accordingly, the second aspect of the present invention includes, as a sub-aspect (B), the use of a compound of formula (I) for the manufacture of a medicament for the treatment of cancer in a pre-selected cancer patient shown to carry an EGFR mutation in the tyrosine kinase domain of the EGF receptor and/or with a tumor harboring an activating HER2 mutation.

Method of Treatment:

The method of treatment according to the invention comprises administration of a therapeutically effective amount of a compound of formula (I), optionally in form of its tautomers, racemates, enantiomers, diastereomers and the mixtures thereof and optionally in form of the pharmacologically acceptable acid addition salts, solvates, hydrates, polymorphs or physiologically functional derivatives thereof, to a patient in need thereof, wherein the active ingredient is administered orally, enterically, transdermally, intravenously, peritoneally or by injection, preferably orally. The patient preferably is a human patient.

Dosage:

The compounds of formula (I) may be administered to the human patient in a daily dose of 0.01-4 mg/kg of body weight (bw), preferably 0.1-2 mg/kg, particularly preferred in a dose of 0.2-1.3 mg/kg bw. For oral treatment the compounds of formula (I) may be administered daily in a total dose of 10, 20, 30, 40, 50, 60, 70, 100, 200, or 300 mg, optionally divided into multiple doses, e.g. 1 to 3 doses to be administered through the day. Preferably the oral daily dose is administered only once a time. These doses can be applied with any of the compounds of formula (I), e.g. with BIBW2992 or an equivalent dose of BIBW2992MA$_2$ containing respective amounts of the active base component. Especially for higher doses periods of treatment should alternate with periods of recovery, without administering the active of formula (I). For instance, treatment could follow a "7 day on-7 day off", a "14 day on-14 day off", a "21 day on 7 day off" or a continuous dosing schedule. "On-off" time periods can be chosen shorter, especially if higher doses are administered, or individually adapted to the needs of the patient. The dosage for intravenous use of a compound of formula (I), e.g. of BIBW2992MA$_2$ may be 1-1000 mg, preferably 5-300 mg, particularly preferred 10-100 mg (dosages refer to the base form BIBW2992), either given as a bolus or, especially if higher doses are applied, as a slow intravenous infusion over several hours, e.g. over about 1, 2, 4, 6, 10, 12 or 24 hours.

In one embodiment the invention relates to the method of treatment described above, characterised in that a compound of formula (I), or its polymorph, metabolite, hydrate, solvate, an individual optical isomer, mixtures of the individual enantiomers or racemates thereof, or a pharmaceutically acceptable salt thereof, is administered intermittent or in a daily dosage such that the plasma level of the active substance preferably lies between 10 and 5000 nM for at least 12 hours of the dosing interval.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

A compound of formula (I), its tautomers, the racemates, the enantiomers, the diastereomers and the mixtures thereof, and optionally the pharmacologically acceptable acid addition salts, solvates, hydrates, polymorphs, physiologically functional derivatives or prodrugs thereof, may be used in monotherapy or combined with other active substances according to the invention, optionally also in conjunction with other pharmacologically active substances.

Pharmaceutical Formulations:

Suitable pharmaceutical preparations for the use in accordance with the invention include, for example, tablets, capsules, suppositories, solutions, and particularly solutions for injection (s.c., i.v., i.m.) and infusion, syrups, emulsions or dispersible powders. The amount of pharmaceutically active compound in each case should be in the range from 0.1-90 wt. %, preferably 0.5-50 wt. % of the total composition, i.e. in amounts which are sufficient to achieve the dosage range given below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of preservatives such as p-hydroxybenzoates, or stabilisers such as alkali metal salts of ethylenediamine tetraacetic acid, optionally using emulsifiers and/or dispersants, while if water is used as the diluent organic solvents may optionally be used as solubilisers or auxiliary solvents, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Suitable excipients may be, for example, water, pharmaceutically acceptable organic solvents, such as paraffins (e.g. petroleum fractions), oils of vegetable origin (e.g. groundnut or sesame oil), mono- or polyfunctional alcohols (e.g. ethanol or glycerol), carriers such as e.g. natural mineral powders (e.g. kaolin, clays, talc, chalk), synthetic mineral powders (e.g. highly dispersed silica and silicates), sugar (e.g. glucose, lactose and dextrose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered in the usual way, preferably by oral or transdermal route, particularly preferably by oral route. When administered orally the tablets may, of course, contain additives, such as e.g. sodium citrate, calcium carbonate and dicalcium phosphate together with various additives, such as starch, preferably potato starch, gelatine and the like, in addition to the abovementioned carriers. Lubricants such as magnesium stearate, sodium laurylsulphate and talc may also be used to form tablets. In the case of aqueous suspensions the active substances may be combined with various flavour enhancers or colourings in addition to the abovementioned excipients. For parenteral use, solutions of the active substances may be prepared using suitable liquid carrier materials.

The following Examples serve to illustrate the invention without restricting it:

Example 1

Molecular Potency and Selectivity of BIBW 2992 Compared to Prior Art Compounds

The data summarized in table 1 were obtained using standard in-solution kinase assays performed at saturating ATP concentrations measuring incorporation of phosphate into poly (GluTyr). The same conditions were used for the different compounds in any kinase assay for direct comparison. IC50 values were generated from 12-point dose-response curves run in triplicates.

TABLE 1

BIBW 2992 is a potent and selective dual inhibitor of the EGFR and HER2 kinases

| Code | EGFR-Kinase [nM] | HER2 Kinase [nM] | $\beta$-InsR Kinase [nM] | VEGFR-2 Kinase [nM] | HGFR Kinase [nM] | c-src Kinase [nM] |
|---|---|---|---|---|---|---|
| gefitinib (ZD-1839) | 3 | 1100 | >100000 | >100000 | >100000 | >100000 |
| erlotinib (OSI-774) | 2 | 238 | >100000 | >100000 | >100000 | >100000 |
| canertinib (CI-1033) | 0.3 | 30 | >100000 | 24900 | >100000 | 1480 |
| lapatinib (GW-2016) | 3 | 15 | >100000 | >100000 | >20000 | >20000 |
| BIBW 2992 | 0.5 | 14 | >100000 | >100000 | 13000 | >4000 |

Example 2

Inhibition of EGF-Induced EGFR, and Constitutive HER2 Receptor Phosphorylation by BIBW 2992, Compared to Prior Art Compounds EC50 values were generated from 12-point dose-response curves. For receptor phosphorylation assays cells were pre-incubated for 1 h with test compound. Cells were then either stimulated with EGF (100 ng/ml for 20 min) or directly harvested and tested for pEGFR or pHER2 by ELISA. Propidium iodide based assays were used to assess the proliferation of BT-474 cells in vitro. The compounds were tested under conditions allowing direct direct comparison.

Dual EGFR/HER2 Inhibition Results in More Potent Inhibition of Cellular Proliferation

TABLE 2

Cellular potency of BIBW 2992

| | Receptor Phosphorylation | | | | |
|---|---|---|---|---|---|
| Compound | A431 EGFR-PO$_4$ EC$_{50}$ [nM] | NIH3T3 HER2-PO$_4$ EC$_{50}$ [nM] | N87 HER2-PO$_4$ EC$_{50}$ [nM] | BT-474 HER2-PO$_4$ EC$_{50}$ [nM] | Proliferation BT-474 EC$_{50}$ [nM] |
| gefitinib (ZD-1839) | 35 | 2300 | 541 | 3710 | 1070 |
| erlotinib (Osi-774) | 5 | 734 | 468 | 930 | 829 |
| canertinib (Cl-1033) | 22 | 85 | 288 | 184 | 66 |
| lapatinib (GW-2016) | 105 | 171 | 101 | 99 | 52 |
| BIBW 2992 | 13 | 71 | 48 | 35 | 12 |

Example 3

Induction of Apoptosis by BIBW 2992

Figure 1:
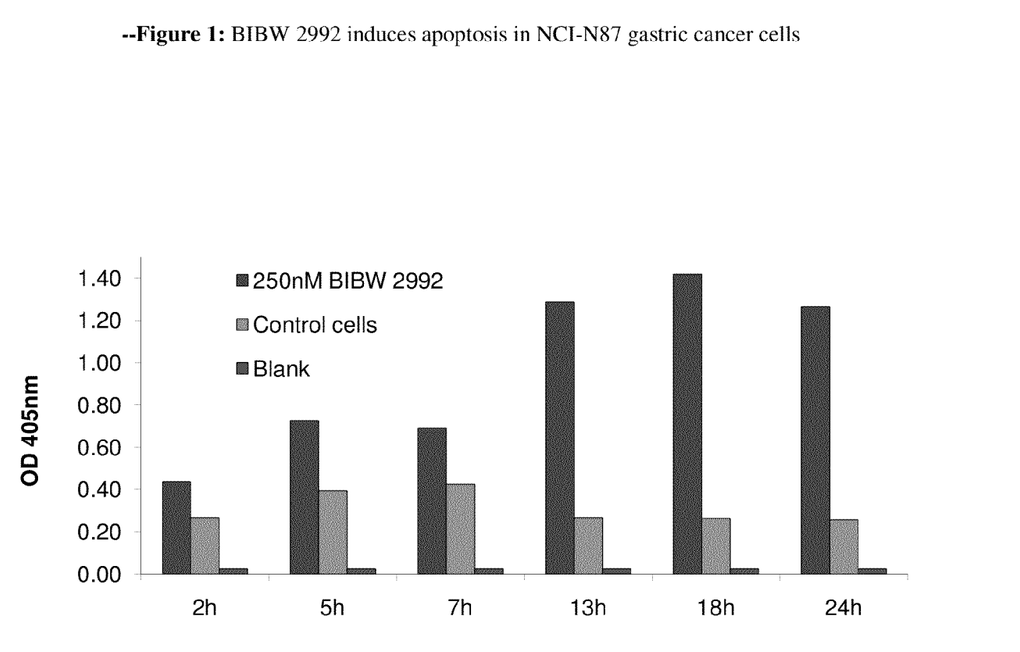
FIG. 1: shows BIBW 2992 induces apoptosis in NCI-N87 gastric cancer cells.

NCI-N87 gastric cancer cells were treated in vitro with 250 nM BIBW 2992. At indicated time points cells were harvested and samples were analyzed for free nucleosomes (apoptosis hallmark) using the Cell death ELISA kit #1774425 from Roche Diagnostics. Results are shown in FIG. 1 (Appendix).

The following Examples show that once daily dosing of BIBW 2992 significantly inhibits, in a dose dependent manner, the growth of a variety of human tumor xenografts in nude mice:

Example 4

Effect of BIBW 2992 on the Growth of Preexisting HNSCC FaDu Xenografts

Figure 2:
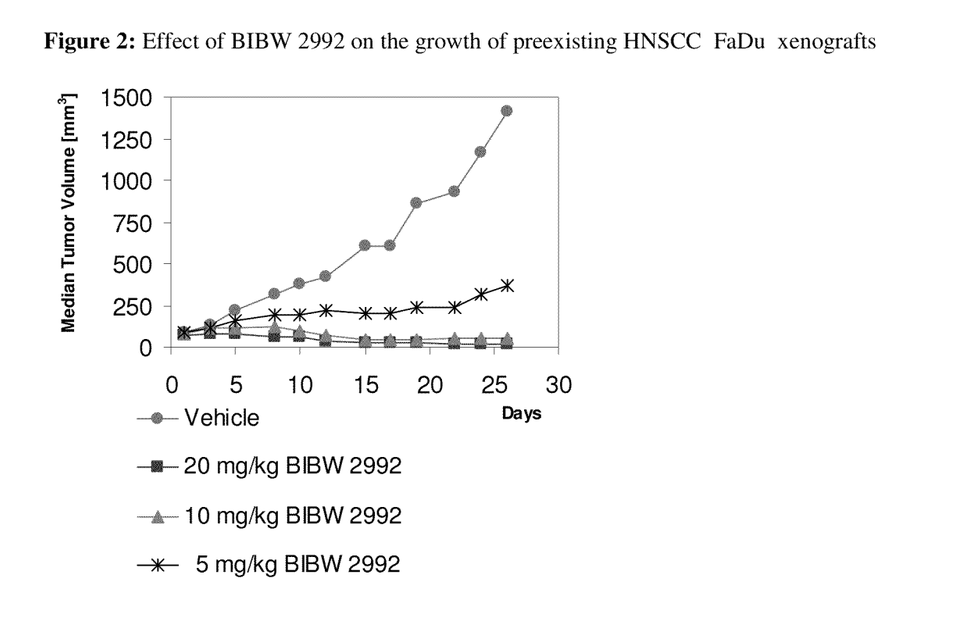
FIG. 2: shows the effect of BIBW 2992 on the growth of preexisting HNSCC FaDu xenografts.

Mice carrying established tumors (50-100 mm3) were treated orally, once daily at indicated doses. On the last day of treatment plasma samples were collected and analyzed for compound levels. Results are shown in FIG. 2 (Appendix).

Example 5

Effect of BIBW 2992 on the Growth of MDA-MB-453 and SKOV-3 Xenografts

Figure 3:
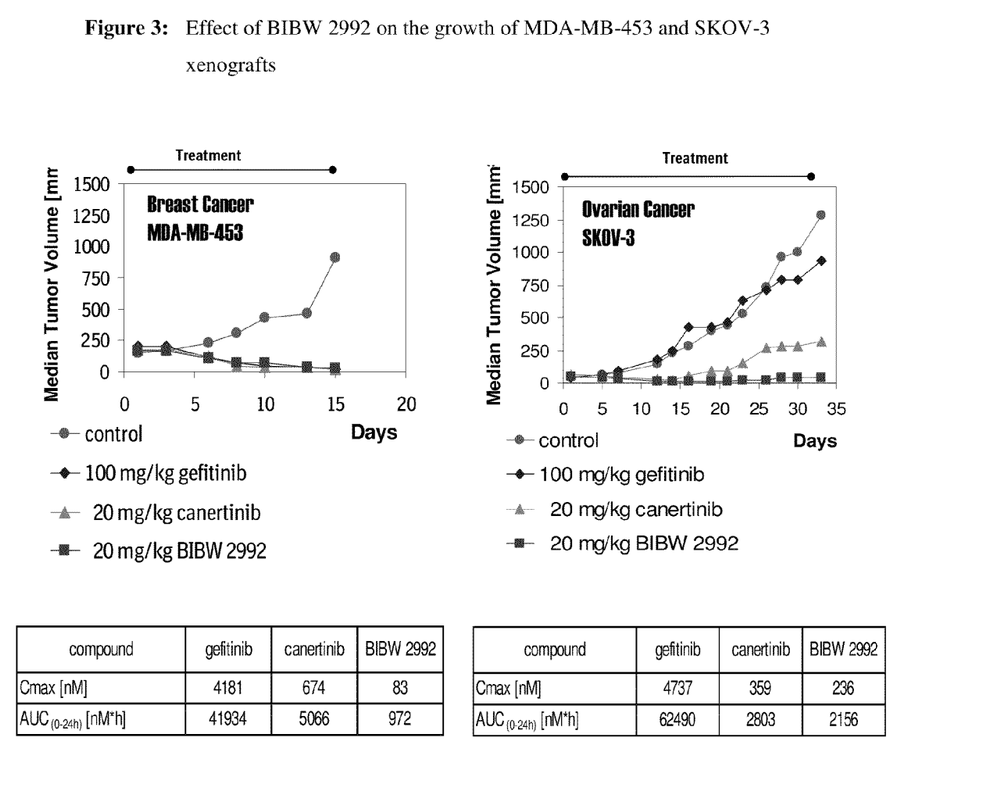
FIG. 3: shows the effect of BIBW 2992 on the growth of MDA-MB-453 and SKOV-3 xenografts.

Mice carrying established tumors (50-100 mm3) were treated orally, once daily at indicated doses with the respective compounds. On the last day of treatment plasma samples were collected and analyzed for compound levels. Results are shown in FIG. 3 (Appendix).

Example 6

Effect of BIBW 2992 on the Growth of Large NCI-N87 Xenografts

Figure 4:
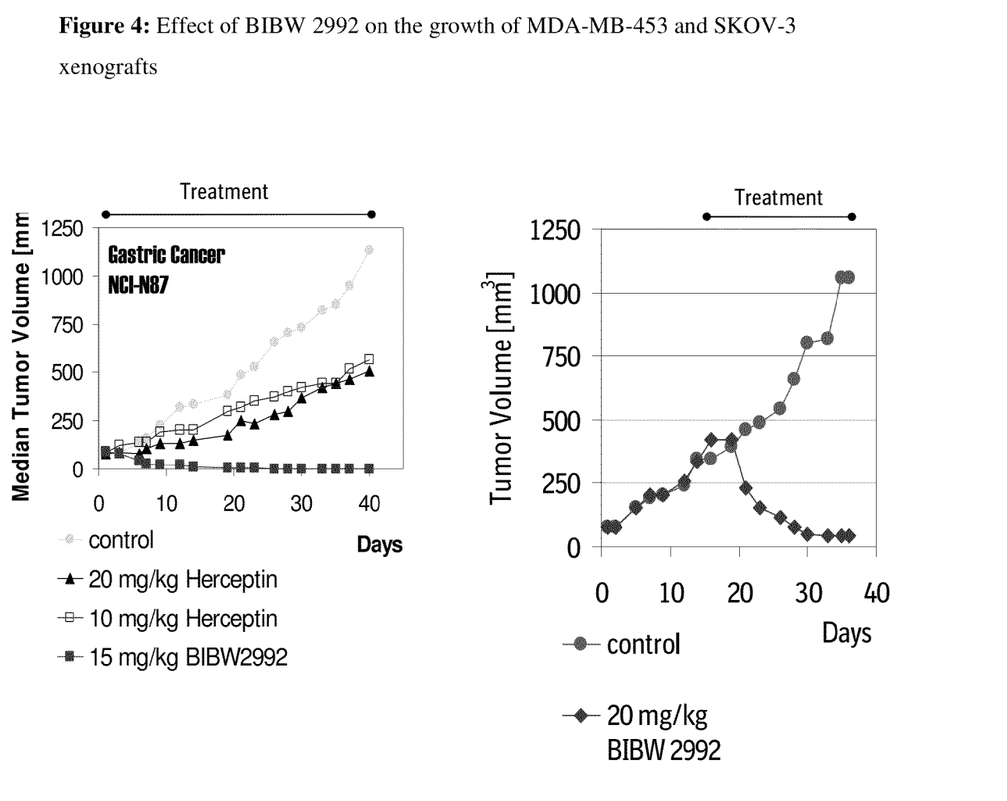
FIG. 4: shows the effect of BIBW 2992 on the growth of MDA-MB-453 and SKOV-3 xenografts.

Mice carrying established tumors (Panel A: 50-100 mm3; Panel B: 450 mm3) were treated once daily p.o. with BIBW 2992 or once weekly i.v. with Herceptin at indicated doses. Daily oral treatment with BIBW 2992 induces regression of NCI-N87 xenografts. Results are shown in FIG. 4 (Appendix).

Example 7

Pharmacodynamic Evaluation of BIBW 2992 in Several Xenograft Models

Mice carrying established tumors (50-100 mm$^3$), were treated orally, once daily at indicated doses with the respective compounds. On the last day of treatment plasma samples were collected and analyzed for compound levels.

Daily oral treatment with BIBW 2992 at a dose of 20 mg/kg results in full anti-tumor activity in various xenograft models. Results are summarized in table 3.

TABLE 3

| Model | Dose [mg/kg/d] | T/C [%] | Cmax [nM] | AUC [nM*h] |
|---|---|---|---|---|
| A431 | 30 | 2 | 587 | 4007 |
| A431 | 20 | 2 | 285 | 3198 |
| SKOV-3 | 20 | 3 | 236 | 2156 |
| MDA-453 | 20 | 3 | 83 | 972 |
| N87 | 20 | 4 | 80 | 1075 |

TABLE 3-continued

| Model | Dose [mg/kg/d] | T/C [%] | Cmax [nM] | AUC [nM*h] |
|---|---|---|---|---|
| SKOV-3 | 15 | 13 | 83 | 589 |
| N87 | 10 | 64 | 66 | 445 |
| A431 | 10 | 80 | 87 | 382 |
| A431 | 3 | 100 | 8 | 21 |

The T/C (Treated/Control) value corresponds to a % of control value: median value in the treated group in relation to median value of tumor size in the control group (usually N = 10) at the end of the experiment, set to 100% (e.g.: a median value in the treated group of 200 mm$^3$ in relation to a median value in the control group of 1000 mm$^3$ results a T/C value of 20%).

Example 8

Response of Patients Treated with BIBW2992

(a) One female patient with metastatic adenocarcinoma of the lung (NSCLC) treated with BIBW2992 MA2 at 10 mg daily (dose refers to the base form; continuous administration schedule) had a confirmed partial response after two months of treatment. The pulmonary lesions have clearly shrunk by >35%, confirmed with a repeat CT scan in 4 weeks. CT scans done in regular intervals confirm the continuation of the partial response. The patient treated developed brain metastases on treatment and increasing the dose of BIBW2992 to 40 mg daily has led to a response in her cerebral disease. This patient remains on treatment 23 months after starting BIBW 2992. This patient's tumour cells have a complex heterozygous EGFR mutation including a deletion and missense mutations of 4-amino acids in the kinase domain, but a wildtype HER2 domain.

(b) Another female patient with non-small cell lung cancer, pleural tumours and mediastinal lymph nodes treated with BIBW2992 MA2 also treated in a continuous dosing schedule at 40 mg daily did develop a partial response as measured by a CT scan after two months of treatment. Five target lesions had been identified; the sum thereof has gone down from 7.3 to 2.6 cm, a decrease of 65%. The patient remains in partial response 14 months after starting treatment with BIBW 2992. An in-frame deletion of 5 amino acids in the same region of the kinase domain has been detected in this patient.

(c) Using a 14 day on 14 day off schedule 2 patients with parotid tumors, one patient with esophageal cancer, one patient with colorectal cancer, one patient with breast cancer, one patient with thyroid cancer and one patient with other endocrine cancer have had stable disease for at least 6 months and have been treated for more than 6 months.

(d) In a continuous dosing schedule and in addition to the above mentioned non-small cell lung cancer patients with partial remissions, a patient with thymic cancer (40 mg daily) and a patient with ovarian cancer (20 mg daily) have had stable disease for at least six months.

(e) In a combined treatment schedule with docetaxel (given every 3 weeks) and BIBW 2992 given for 3 days after the administration of docetaxel one patient had a complete response (breast cancer) and one had partial response (oesophageal).

(f) In a combined treatment schedule with docetaxel (given every 3 weeks) and BIBW 2992 given for 20 or 13 days after the administration of docetaxel, two patients had a partial responses (ovarian and non-small cell lung cancer).

Example 9

Coated Immediate-Release Tablets Containing 75 mg of Active Substance by Dry-Granulation Process Composition:
1 tablet contains:

| | |
|---|---|
| active substance | 75.0 mg |
| calcium phosphate anhydrous | 108.0 mg |
| corn starch | 35.5 mg |
| polyvinylpyrrolidone | 10.0 mg |
| magnesium stearate | 1.5 mg |
| hydroxypropylmethylcellulose | 7.5 mg |
| polyethylene glycol | 1.0 mg |
| polydextrose | 5.0 mg |
| talc | 1.0 mg |
| pigments | 0.5 mg |
| water (volatile) | |
| | 245.0 mg |

Preparation:

The active substance is mixed with calcium phosphate, corn starch, polyvinylpyrrolidone, hydroxypropylmethylcellulose and half the specified amount of magnesium stearate. Ribbons are produced in a roller-compactor and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg

Tablet shape: 9 mm round, bi-convex

The tablet cores are subsequently coated with an aqueous film-coat consisting essentially of hydroxypropylmethylcellulose, polyethylene glycol, polydextrose, talc and pigments.

Weight of coated tablet: 245 mg.

Example 10

Extended-Release Tablets Containing 100 mg of Active Substance by Organic Granulation Granulation Process 1 tablet contains:

| | |
|---|---|
| active substance | 100.0 mg |
| lactose | 34.0 mg |
| hydroxypropylmethylcellulose | 80 mg |
| polyvinylpyrrolidone | 4.0 mg |
| magnesium stearate | 2.0 mg |
| ethanol (volatile) | |
| | 220.0 mg |

Preparation:

The active substance, lactose and hydroxypropylmethylcellulose are mixed together and uniformly moistened with solution of the polyvinylpyrrolidone in ethanol. After the moist composition has been screened (2.0 mm mesh size) and dried in a rack-type drier at 50° C. it is screened again (1.5 mm mesh size) and the lubricant is added. The final blend is compressed to form tablets.

Weight of tablet: 220 mg

Tablet shape: 10 mm, flat-faced, with bevelled edges.

Example 11

Tablets Containing 150 mg of Active Substance by Aqueous Granulation Process 1 tablet contains:

| | |
|---|---|
| active substance | 150.0 mg |
| powdered lactose | 98.0 mg |
| corn starch | 40.0 mg |
| colloidal silica | 1.0 mg |
| polyvinylpyrrolidone | 10.0 mg |
| magnesium stearate | 1.0 mg |
| | 300.0 mg |

Preparation:

The active substance mixed with lactose, corn starch is moistened with a 20% aqueous polyvinylpyrrolidone solution and passed through a screen with a mesh size of 1.5 mm. The granules, dried at 45° C., are passed through the same screen again and mixed with the specified amount of magnesium stearate and colloidal silica. Tablets are pressed from the final blend.

Weight of tablet: 300 mg

Tablet shape: 14 mm×6.8 mm, oblong biconvex with embossment

Example 12

Hard Capsules Containing 150 mg of Active Substance in Granules

Composition:
1 capsule contains:

| | |
|---|---|
| active substance | 150.0 mg |
| microcrystalline cellulose | 80.0 mg |
| lactose (spray-dried) | 87.0 mg |
| colloidal silica | 10.0 mg |
| | 320.0 mg |

Preparation:

The active substance is mixed with the excipients in a high-shear mixer, passed through a screen with a mesh size of 0.75 mm and homogeneously mixed using a suitable apparatus. The finished mixture is packed into size 1 hard gelatin capsules.

Capsule filling: 320 mg

Capsule shape: size 1, opaque hard capsule.

Example 13

Hard Capsules Containing 150 mg of Active Substance as a Liquid Fill

Composition:
1 capsule contains:

| | |
|---|---|
| active substance | 150.0 mg |
| groundnut oil | 300.0 mg |
| colloidal silica | 10.0 mg |
| | 460.0 mg |

Preparation:

The active substance is dissolved in the excipient inside a homogenizer and the colloidal silica is added for adjustment of viscosity. The finished mixture is filled into size 1 hard gelatin capsules.

Capsule filling: 460 mg

Capsule shape: size 0, opaque hard capsules.

Example 14

Suppositories Containing 150 mg of Active Substance
Composition:
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously suspended therein and the melt is poured into chilled moulds.

Example 15

Suspension Containing 50 mg of Active Substance

Composition:
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100.0 ml |

Preparation:
The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.
5 ml of suspension contain 50 mg of active substance.

Example 16

Ampoules Containing 10 mg Active Substance

Composition:
1 ampoule contains:

| | |
|---|---|
| active substance | 10.0 mg |
| 0.01 N hydrochloric acid. | q.s |
| sodium chloride | q.s. |
| double-distilled water ad | 2.0 ml |

Preparation:
The active substance is dissolved in the requisite amount of 0.01N HCl, made isotonic with sodium chloride, filtered sterile and transferred into 2 ml ampoules with subsequent steam sterilization.

Example 17

Ampoules Containing 50 mg of Active Substance

Composition:
1 ampoule contains:

| | |
|---|---|
| active substance | 50.0 mg |
| 0.01 N hydrochloric acid | q.s. |
| sodium chloride | q.s. |
| double-distilled water ad | 10.0 ml |

Preparation:
The active substance is dissolved in the necessary amount of 0.01N HCl, made isotonic with sodium chloride, filtered sterile and transferred into 10 ml ampoules with subsequent steam sterilization.

Example 18

Capsules for Powder Inhalation Containing 5 mg of Active Substance
Composition:
1 capsule contains:

| | |
|---|---|
| active substance | 5.0 mg |
| lactose for inhalation | 15.0 mg |
| | 20.0 mg |

Preparation:
The active substance is mixed with lactose for inhalation. The mixture is packed into capsules in a capsule-making machine (weight of the empty capsule approx. 50 mg).
weight of capsule: 70.0 mg
size of capsule 3

Example 19

Solution for Inhalation for Hand-Held Nebulisers Containing 2.5 mg Active Substance
Composition:
1 spray contains:

| | |
|---|---|
| active substance | 2.500 mg |
| benzalkonium chloride | 0.001 mg |
| 1N hydrochloric acid q.s. | 2.500 mg |
| ethanol/water (50/50 m/m) ad | 15.000 mg |

Preparation:
The active substance and benzalkonium chloride are dissolved in ethanol/water (50/50). The pH of the solution is adjusted with 1N hydrochloric acid. The resulting solution is filtered sterile and transferred into suitable containers for use in hand-held nebulisers (cartridges).
Contents of the container: 4.5 g

The invention claimed is:
1. A method for treating head and neck squamous cell carcinoma in a patient, the method comprising administering a therapeutically effective amount of an EGFR inhibitor to the patient wherein said inhibitor is the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a physiologically acceptable salt thereof.

2. The method according to claim 1, wherein the Head and neck squamous cell carcinoma is selected from the group consisting of lip and oral cavity cancer, laryngeal cancer, nasopharyngeal cancer, oropharyngeal cancer and hypopharyngeal cancer.

3. The method according to claim 1 or 2, wherein the compound is
- (d') 4-[3-chloro-4-fluorophenyl)amino]-6-{[4-(N,N-dimethylamino)-1-oxo-2-buten-1-yl]amino}-7-((S)-tetrahydrofuran-3-yloxy)-quinazoline dimaleate.

\* \* \* \* \*